(12) United States Patent
Carson

(10) Patent No.: US 6,799,063 B2
(45) Date of Patent: Sep. 28, 2004

(54) TEMPERATURE CONTROL PADS WITH INTEGRAL ELECTRODES

(75) Inventor: Gary Allen Carson, Golden, CO (US)

(73) Assignee: Medivance Incorporated, Louisville, CO (US)

( * ) Notice: Subject to any disclaimer, the term of this patent is extended or adjusted under 35 U.S.C. 154(b) by 20 days.

(21) Appl. No.: 10/087,389

(22) Filed: Feb. 27, 2002

(65) Prior Publication Data

US 2003/0163185 A1 Aug. 28, 2003

(51) Int. Cl.$^7$ ................................................ A61B 5/00
(52) U.S. Cl. ..................................... 600/372; 607/152
(58) Field of Search ............................... 600/372–397; 607/96–156

(56) References Cited

U.S. PATENT DOCUMENTS

| | | | |
|---|---|---|---|
| 3,867,939 A | 2/1975 | Moore et al. ................ 128/294 |
| 3,995,621 A | 12/1976 | Fletcher et al. ................ 128/2 |
| 4,108,146 A | 8/1978 | Golden ........................ 128/400 |
| 4,118,946 A | 10/1978 | Tubin ........................... 62/514 |
| 4,140,130 A | * 2/1979 | Storm | |
| 4,149,541 A | 4/1979 | Gammons et al. .......... 128/400 |
| 4,154,245 A | 5/1979 | Daily ........................... 128/400 |
| 4,887,614 A | * 12/1989 | Shirakami et al. | |
| 4,919,134 A | 4/1990 | Streeter ...................... 128/400 |
| 4,962,761 A | 10/1990 | Golden ........................ 128/400 |
| 5,097,829 A | 3/1992 | Quisenberry ............... 128/400 |
| 5,124,107 A | 6/1992 | Schmid ....................... 264/255 |
| 5,143,071 A | 9/1992 | Keusch et al. .............. 128/640 |
| 5,300,103 A | 4/1994 | Stempel et al. ............. 607/108 |
| 5,304,213 A | 4/1994 | Berke et al. ................. 607/104 |
| 5,383,919 A | 1/1995 | Kelly et al. ................. 607/104 |
| 5,470,353 A | 11/1995 | Jensen ......................... 607/104 |
| 5,486,207 A | 1/1996 | Mahawili .................... 607/104 |
| 5,514,169 A | 5/1996 | Dickerhoff et al. ......... 607/107 |
| 5,520,180 A | 5/1996 | Uy et al. ..................... 128/640 |
| 5,545,194 A | 8/1996 | Augustine ................... 607/104 |
| 5,609,620 A | 3/1997 | Daily .......................... 607/105 |
| 5,647,871 A | 7/1997 | Levine et al. ................. 606/45 |

(List continued on next page.)

OTHER PUBLICATIONS

Vermont Medical, Inc., "Quality Cardiac Monitoring and Diagnostic Electrodes", Publication Date Unknown, 1 Page.
Kimberly–Clark Corporation, "Multifunction Cardiac Electrodes", Publication Date Unknown, 2 Pages.

*Primary Examiner*—Scott M. Getzow
(74) *Attorney, Agent, or Firm*—Marsh Fischmann & Breyfogle LLP

(57) ABSTRACT

A dual function medical pad is disclosed for both controlling patient temperature and providing a patient-to-electrode interface. The pad includes a fluid containing layer for containing a thermal exchange fluid circulated therethrough, wherein the medical pad is operable for thermal exchange with a patient through a first side of the fluid containing layer. One or more electrodes are interconnected to the fluid containing layer on the first side (e.g. electrosurgical return electrode(s), EKG electrode(s), pacing/defribullation electrode(s)). Preferably, an electrical connector is electrically connected to the electrode and extends through the fluid containing layer to a second side thereof. Such electrical connector is interconnected or selectively interconnectable to a signal cable. The pad may further include an adhesive surface which extends over at least a portion of the first side of the fluid containing layer. Preferably, the adhesive surface substantially covers the electrode(s). The adhesive surface may be defined by a conformable layer that is thermally and electrically conductive. Such conformable layer may comprise a first material suspended in a matrix defined by a second material (e.g. a liquid suspended in a polymer matrix).

39 Claims, 6 Drawing Sheets

U.S. PATENT DOCUMENTS

| | | | |
|---|---|---|---|
| 5,658,325 A | 8/1997 | Augustine | 607/107 |
| 5,678,545 A | 10/1997 | Stratbucker | 128/640 |
| 5,733,318 A | 3/1998 | Augustine | 607/104 |
| 5,830,214 A | 11/1998 | Flom et al. | 606/41 |
| 5,846,558 A | 12/1998 | Nielsen et al. | 424/448 |
| 5,887,437 A | 3/1999 | Maxim | 62/4 |
| 5,913,849 A | 6/1999 | Sundström et al. | 604/291 |
| 6,074,389 A | 6/2000 | Levine et al. | 606/45 |
| 6,117,164 A | 9/2000 | Gildersleeve et al. | 607/108 |
| 6,135,953 A | 10/2000 | Carim | 600/372 |
| 6,149,620 A | 11/2000 | Baker et al. | 604/22 |
| 6,171,304 B1 | 1/2001 | Netherly et al. | 606/32 |
| 6,197,045 B1 | 3/2001 | Carson | 607/104 |
| 6,206,876 B1 | 3/2001 | Levine et al. | 606/45 |
| 6,232,366 B1 | 5/2001 | Wang et al. | 523/111 |
| 6,238,427 B1 | 5/2001 | Matta | 607/104 |
| 6,240,323 B1 | 5/2001 | Calenzo, Sr. et al. | 607/142 |

* cited by examiner

TEMPERATURE CONTROL PADS WITH INTEGRAL ELECTRODES

FIELD OF THE INVENTION

The present invention relates to medical pads, and more particularly, to dual-function pads for both controlling patient temperature and providing a patient-to-electrode interface.

BACKGROUND OF THE INVENTION

Increasingly, medical pad systems are being employed to achieve thermal exchange with patients. In such systems, a fluid (e.g. air or water) is circulated through one or more pads which are contacted with a patient to effect surface-to-surface thermal energy exchange. As may be appreciated, the effectiveness of such thermal exchange is largely dependent upon the extent and intimacy of skin contact, as well as the maintenance of a desired thermal gradient across the thermal exchange region.

To date, medical thermal energy exchange pads have largely been employed to address emergency hypothermia or hyperthermia patient conditions. More recently, it has also been recognized that such medical pads may be employed in conjunction with surgical procedures where selective thermal regulation of a patient is desirable.

Many of these surgical procedures entail the utilization of external electrodes for transcutaneous electrical energy receipt/transmission. By way of example, electrodes are utilized in electrosurgical procedures, electrocardiogram (EKG) monitoring, and pacing/defibrillation therapy. In each of these applications a reliable electrode-to-patient interface is of importance.

Of note, such electrode-to-skin interfaces are often located in bodily regions where medical thermal energy exchange pad contact is also desired. As such, electrode and thermal energy exchange pad placement procedures and corresponding interconnections can become complicated. Further, the efficacy of thermal regulation can be compromised.

SUMMARY OF THE INVENTION

Accordingly, a primary objective of the present invention is to provide a medical pad that facilitates the placement and utilization of componentry for both effective patient thermal regulation and one or more external electrode-to-patient interface(s).

Another objective of the present invention is to enhance the reliability of external electrode-to-patient interfaces.

Yet a further objective of the present invention is to enhance patient comfort while providing both a thermal energy exchange and electrode interface with a patient.

The above objectives and additional advantages may be realized by the medical pad disclosed hereinbelow. The inventive pad includes a fluid containing layer for containing a thermal exchange fluid circulated therethrough, wherein the medical pad is operable for thermal exchange with a patient through a first side of the fluid containing layer. The medical pad further includes at least one external electrode interconnected to the fluid containing layer on the first side thereof. As may be appreciated, the "external electrode" may be of any type that is intended or otherwise adapted to transcutaneously receive electrical energy (e.g. for medical monitoring, therapeutic or electrosurgical purposes).

The integration of a fluid containing layer and an external electrode into the same medical pad yields a number of advantages. For example, positioning of the fluid containing layer and of the external electrode may be achieved in tandem. Additionally, skin contact can be optimized within a given area, thereby enhancing thermal regulation capabilities. Further, an integrated pad approach reduces interference between interconnected componentry associated with the electrode and fluid containing layer during set-up and use.

In this regard, the inventive medical pad may further comprise an electrical connector electrically connected to the electrode and extending through the fluid containing layer to a second side thereof. In turn, the electrical connector may be interconnected with an electrical cable for electrical signal transmission (e.g. to a monitor, etc.). In one arrangement, the electrical connector may include a port (e.g. disposed in opposing relation to the electrode) for selective interconnection/disconnection with an electrical cable. Such arrangement further facilitates pad positioning and set-up operations.

The electrical connector may be located to extend through the second side of the fluid containing layer at an exit location that provides ready-access when the pad is positioned on a patient. Relatedly, the exit location may be selected so that it is not interposed between a support surface and a patient during use. For example, in a medical pad intended for contacting the back of a prone patient facing upward, the exit location may be provided within a predetermined pad area that is located immediately adjacent to the side of a patient when utilized.

To isolate the electrical connector, an insulator should surround the electrical connector as it extends through the fluid containing layer. Such insulator may be integrally defined by a backing member comprising the medical pad. More particularly, the fluid containing layer may comprise a sheet-like member adjoined to a backing member, wherein the backing member includes integral protruding ribs and/or dimples which define fluid flow channels that extend between fluid inlet and fluid outlet ports. One or more of such dimples or ribs may be disposed to act as an insulator surrounding an for the electrical connector.

As may be appreciated, the inventive medical pad may comprise one or a plurality of different external electrodes each interconnected to the fluid circulation layer on the first side thereof. Such electrodes may be located in relation to their corresponding intended functions. By way of example, the electrode(s) may be one of a group consisting of the following:

an electrosurgical return electrode;
a defibrillation electrode;
an electrocardiogram (EKG) electrode; and,
a pacing electrode.

Each of the noted electrode types provide electrical circuit return paths from a patient to a monitor or the like. As such, a reliable electrode-to-patient interface is desirable.

For such purposes, and to further provide for high-efficiency thermal transfer with a patient, the inventive pad may comprise an adhesive surface extending over at least a portion, and preferably a major portion, of the first side of the fluid circulation layer for contact with a patient. Preferably, the adhesive surface also extends over and about at least a portion of the electrode(s) to yield a substantially continuous surface for patient contact and a reliable electrode interface. By way of example, the adhesive surface may have a peel value against the skin of a patient of at least about 10 g/in. A release liner may be provided over the adhesive surface for selective removal prior to patient use.

In a primary embodiment, the adhesive surface may be defined by a conformable layer which is both thermally and electrically conductive. Preferably, the electrode(s) is located, or captured, between the conformable layer and the fluid circulation layer, wherein a pliable laminate assembly is provided for patient engagement. To enhance electrical energy receipt, the conformable layer may advantageously cover, surround and extend laterally away from the electrode (s). Again, a conformable layer that covers a major portion, if not all, of the patient facing side of the pad is preferred.

To yield the noted conductive attributes, the conformable layer may comprise a first material suspended in a matrix defined by a second material. More particularly, the first material may comprise a conductive liquid while the second material may comprise a polymer. In one arrangement, the first and second materials are defined by a hydrogel. To enhance electrical conductivity, the conformable layer may further comprise an electrically conductive additive. By way of example, such additive may be an electrolyte that is included in a liquid solution, including magnesium chloride, sodium chloride, ammonium acetate, magnesium acetate, and magnesium sulfate.

In conjunction with the noted features, the inventive medical pad may incorporate further teachings of U.S. Pat. No. 6,197,045 entitled "COOLING/HEATING PAD AND SYSTEM", and U.S. patent application Ser. No. 09/476,850 entitled "COOLING/HEATING PAD AND SYSTEM", filed Jan. 3, 2000, each hereby incorporated by reference in its entirety.

Additional aspects and advantages of the present invention will become apparent to those skilled in the art upon consideration of the further description provided hereinbelow.

DETAILED DESCRIPTION

Figure 1:
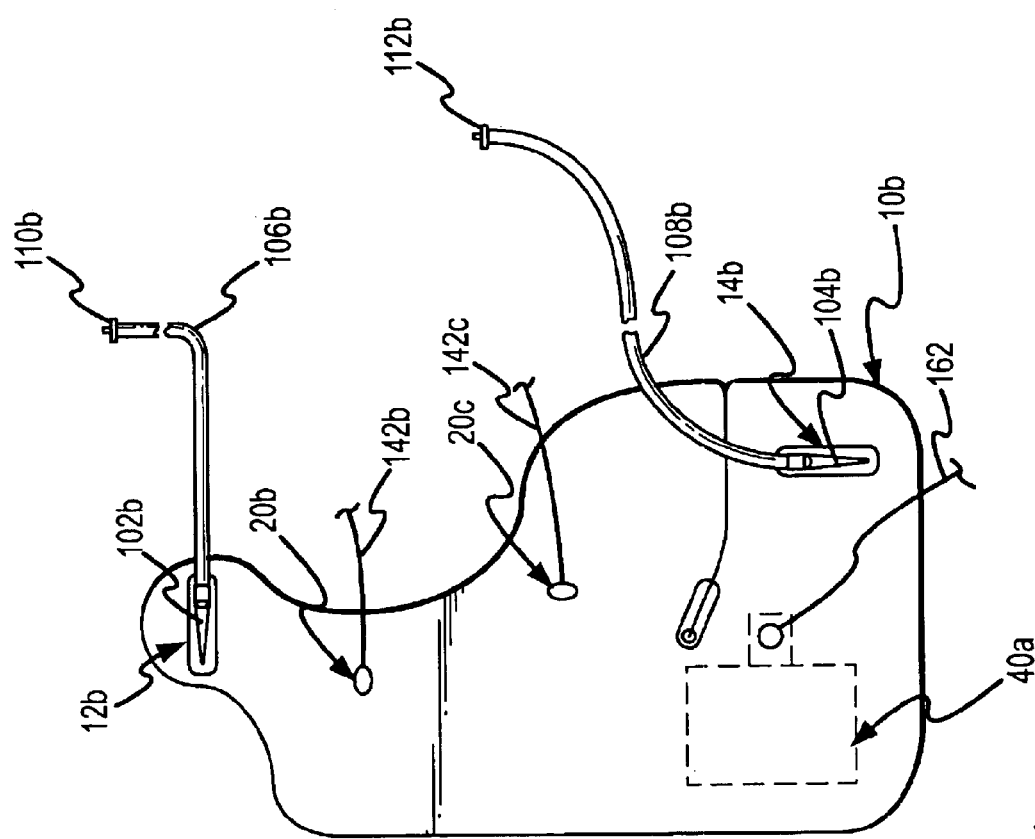
FIG. 1 illustrates right and left back pad embodiments of the present invention.
Figure 1:
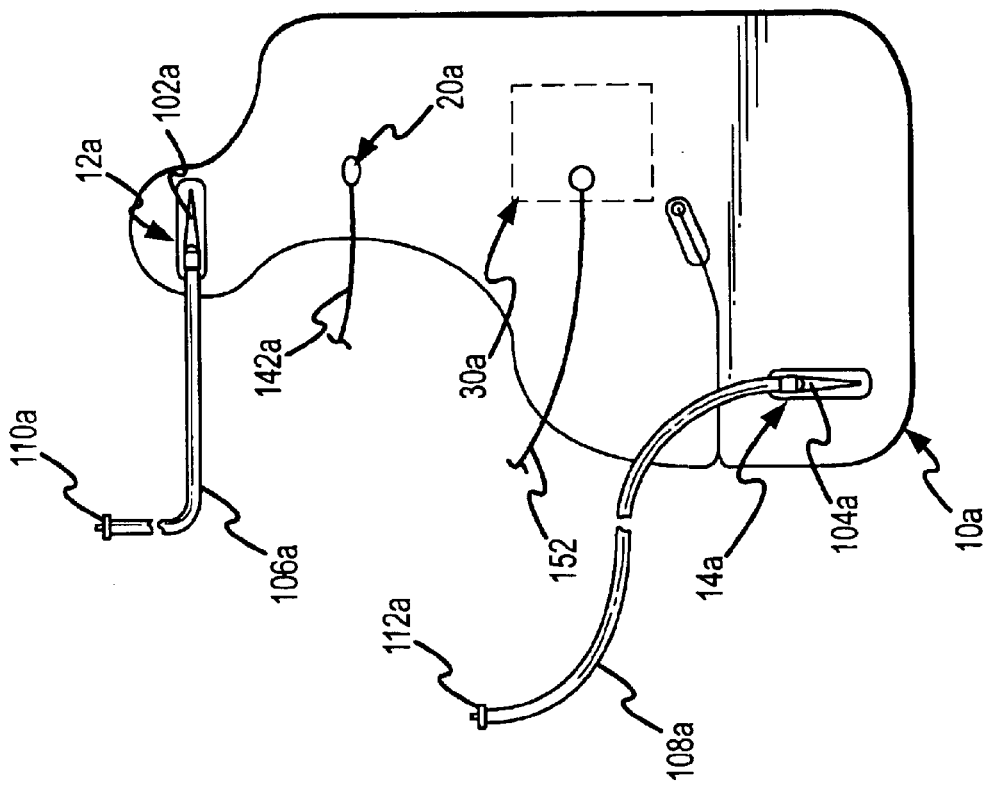
Figure 2:
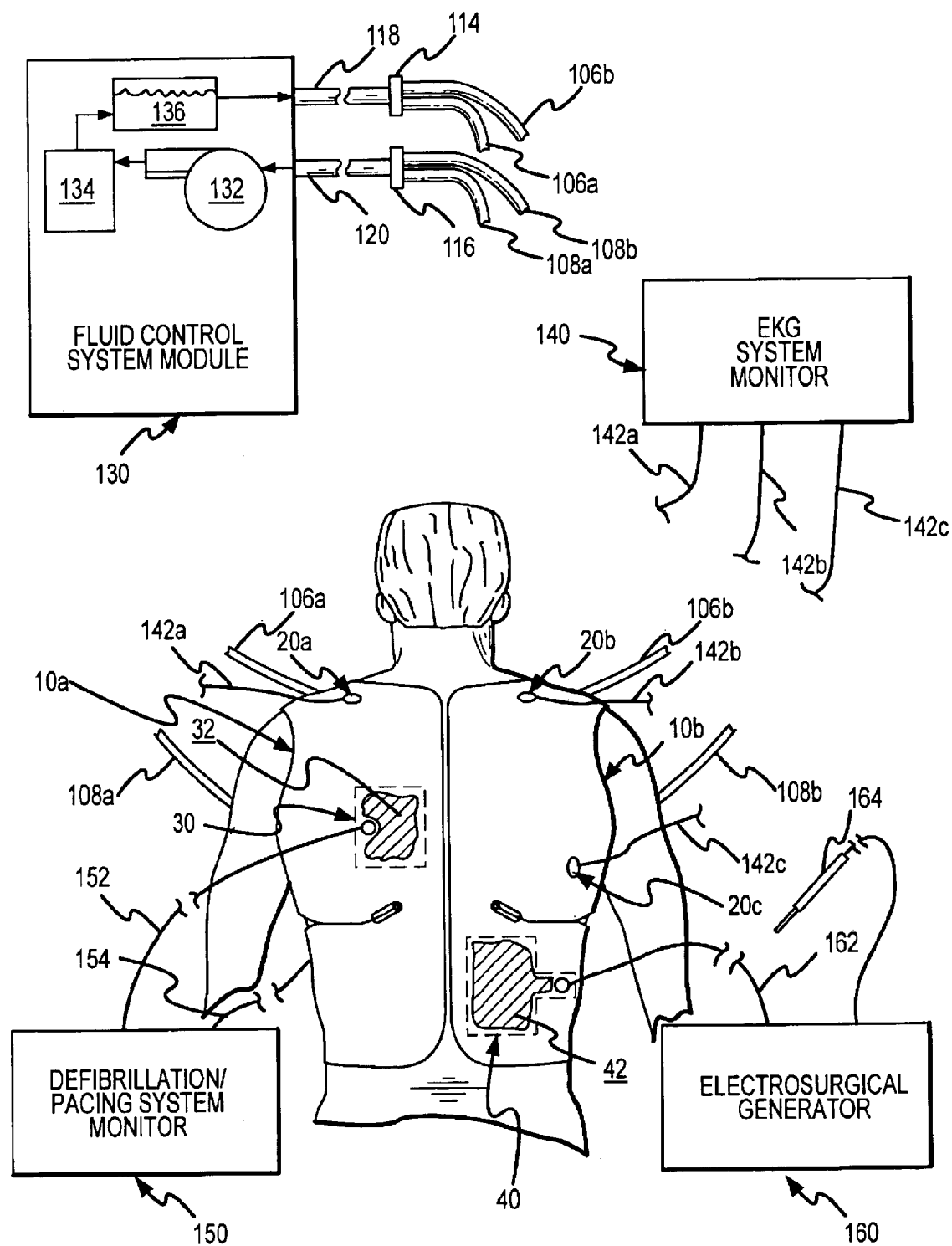
FIG. 2 illustrates the back pad embodiments of FIG. 1 applied to a patient and interconnected to fluid control and electrode interface systems, wherein selected electrode-containing portions of the pads are shown in a partial cutaway manner.

FIG. 1 illustrates right and left back pad embodiments of the invention which comprise various optional features. FIG. 2 illustrates the back pad embodiments of FIG. 1 as applied to a patient and interconnected to a fluid-control system and various alternative systems that utilize patient-to-external electrode interfaces. Of note, the present invention is not limited to back pad applications and may be employed in conjunction with pads intended for contact interface with other bodily portions, including for example leg pads, arm pads and head pads.

As illustrated in FIGS. 1 and 2, the right and left back pads 10a, 10b include fluid inlet ports 12a, 12b and fluid outlet ports 14a, 14b, having port members 102a, 102b and 104a, 104b, respectively, which are interconnected to one end of fluid tubing lines 106a, 106b and 108a, 108b, respectively. In turn, tubing lines 106a, 106b and 108a, 108b are provided with connectors 110a, 110b and 112a, 112b for selective interconnection with manifolds 114 and 116, respectively, which are interconnected or selectively interconnectable to outlet and inlet ports 118 and 120, respectively, of a fluid-control system module 130.

The fluid-control system module 130 may comprise a number of components for circulating thermally-regulated fluid through the back pads 10a, 10b. By way of primary example, fluid-control system module 130 may comprise of a fluid pump 132 having an inlet side interconnected to inlet port 120 for drawing fluid through the back pads 10a, 10b under negative pressure. The outlet side of fluid pump 132 may be fluidly interconnected to a heating/cooling unit 134. In turn, the heating/cooling unit 134 may be fluidly interconnected to one or more fluid reservoirs 136 that are fluidly interconnected to the fluid outlet port 118.

As further shown in FIGS. 1 and 2, the back pads 10a, 10b may include a number of alternative electrode assemblies for patient interface. By way of example, EKG electrode assemblies 20a, 20b and 20c may be interconnected to the back pads 10a, 10b at predetermined locations appropriate for bodily interface upon application of the back pads 10a, 10b to a patient. In turn, interconnection cables 142a, 142b and 142c may be utilized to interconnect the EKG electrode assemblies 20a, 20b and 20c, respectively, with an EKG system monitor 140.

Right back pad 10a may further include a defibrillation or pacing electrode 30. As illustrated in the cutaway window region, electrode assembly 30 may include an electrode 32 for patient interface proximal to a patient's heart. Electrode assembly 30 may be interconnected via cabling 152 to a defibrillation/pacing system monitor 150. In turn, cabling 154 may be interconnected between system monitor 150 and an implanted pacemaker (not shown).

Left back pad 10b may comprise an electrosurgical return electrode assembly 40. As illustrated by the cutaway window, electrode assembly 40 may include an electrode 42 for patient interface proximal to a patient's lower abdominal region. The electrode assembly may be interconnected via cabling 162 to an electrosurgical generator 160. In turn, an electrosurgical pencil 164 may be interconnected to generator 160. As shown in FIG. 2, electrode assembly may be provided with an extending leg portion (e.g. the base leg of a T-shaped configuration) that extends to the side of a patient (e.g. outside a region through which the patient may be supported during surgery). In turn, an exposed portion (e.g. a connector port as described below) of assembly 40 may be readily accessed for interconnection with cabling 162.

As may be appreciated, the integration of one or more electrode assemblies into back pads 10a, 10b allows the electrodes of such assemblies to be operatively interfaced with a patient contemporaneous with the positioning of pads 10a, 10b on the patient, thereby facilitating set-up procedures. Further, as illustrated by FIGS. 1 and 2, interconnection of the various electrode assemblies to their corresponding monitors, etc. is facilitated since the electrode assemblies include exposed portions (e.g. connector ports as described below) that are readily accessible when pads 10a, 10b are positioned on a patient.

Figure 3A:
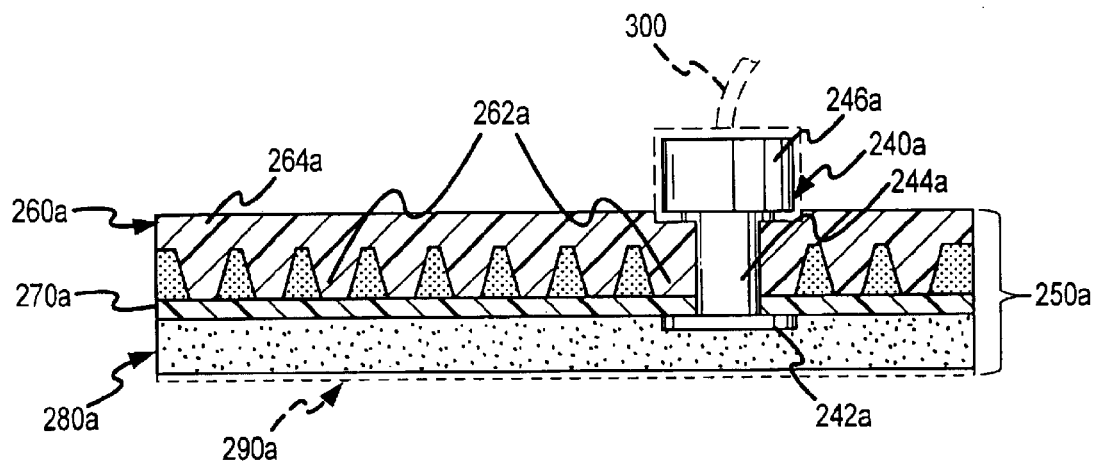
FIGS. 3A and 3B illustrate side cross-sectional views of alternate medical pad embodiments of the present invention.
Figure 3B:
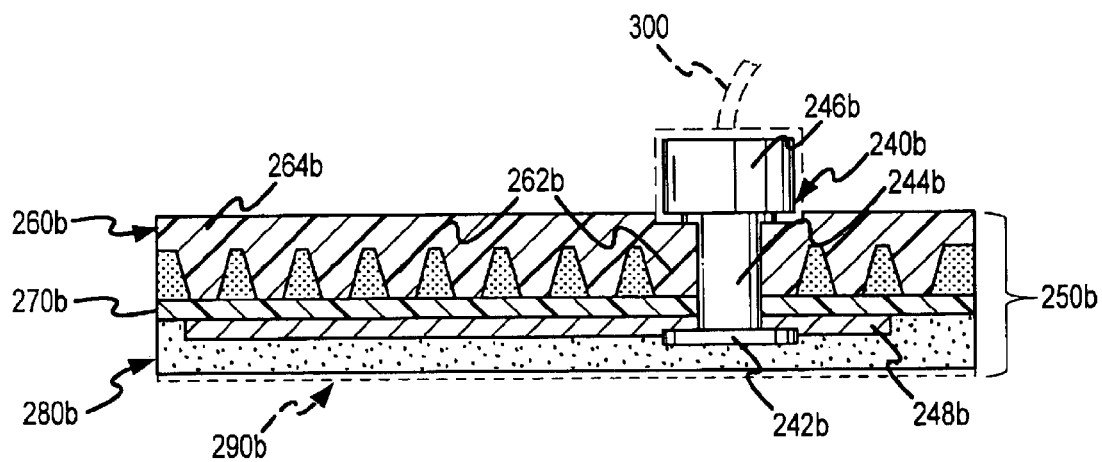

In that regard, reference is now made to FIGS. 3A and 3B which illustrate alternate medical pad embodiments 210a, 210b. As shown, the embodiments 210a, 210b include corresponding electrode assemblies 240a, 240b integrated in laminated pad assemblies 250a, 250b, respectively. The laminated pad assemblies 250a, 250b may be of a construction as disclosed in U.S. Pat. No. 6,197,045 entitled "COOLING/HEATING PAD AND SYSTEM", and U.S. patent application Ser. No. 09/476,850 entitled "COOLING/ HEATING PAD AND SYSTEM", filed Jan. 3, 2000, each hereby incorporated by reference in its entirety.

In the embodiment of FIG. 3A the laminated pad assembly 250a includes opposing first and second members 260a, 270a which are adjoined to define a fluid containing layer therebetween. Similarly, the laminated pad assembly 250b of the FIG. 3B embodiment includes first and second members 260b, 270b adjoined to define a fluid containing layer therebetween. Such fluid containing layers may be provided with defined channels, or passageways, for fluid flow between inlet and outlet ports which are interconnectable with a fluid control system, such as module 10 shown in FIG. 2.

By way of example, first members 260a, 260b may include rib and/or dimple members 262a, 262b interconnected to and extending away from a backing layer 264a, 264b, respectively. The rib members may define fluid flow channels through the fluid containing layers. Further, the ribs and dimple members 262a, 262b may function to support thin sheet-like layers defining second members 270a, 270b, respectively.

In one example, first members 260a, 260b (e.g. including rib and dimple members 262a, 262b) may be integrally defined by a thermal-molded material such as polyethylene, polyurethane, polyvinyl chloride, and most preferably, ethylene-acetate copolymers. The material may be provided in the form of an insulating, closed cell foam having a density of about 2 to 12 lbs./ft$^3$. In this regard, and as further discussed below, the first members 260a, 26b may integrally provide an insulating member(s) (e.g. ribs, dimples, etc.) that surround and desolate electrical connectors that extend through the fluid containing layers. The fabrication process may comprise injection molding, vacuum forming, compression molding or the like. In conjunction with the noted example, second members 262a, 262b may be defined by a non-porous film, such as a polyurethane, polyvinyl chloride, polypropylene or nylon film.

Referring further now to FIGS. 3A and 3B it can be seen that laminated pad assemblies 250a, 250b further include conformable layers 280a, 280b, respectively. The conformable layers 280a, 280b may comprise a conductive liquid (e.g. water) suspended in a polymer matrix. By way of example, the conformable layers 280a, 280b may be defined by a hydrogel material. As may be appreciated, the conformable layers 280a, 280b are thermally and electrically conductive to function as a means for both thermal transfer between the fluid containing layers and a patient, as well as electrical energy transfer between electrode assemblies 240a, 240b and a patient. To further enhance electrical energy transmission, the conformable layers 280a, 280b may also include an electrolyte additive, e.g. magnesium chloride, sodium chloride, ammonium acetate, magnesium acetate, and magnesium sulfate.

Of note, the conformable layers 280a, 280b also provide an adhesive surface across the lateral extent thereof, and preferably across a major portion of the medical pads in which assemblies 250a, 250b are provided, for selective, conformal and secure pad attachment to the skin of a patient. Such an adhesive surface may be defined in other arrangements by an adhesive material that is disposed directly upon patient-facing surfaces of second members 270a, 270b and/ or electrode assemblies 240a, 240b. In the embodiments shown in FIGS. 3A and 3B, optional release liners 290a, 290b may be provided over the adhesive surface of conformable layers 280a, 280b for selective removal immediately prior to patient application.

The electrode assemblies 240a, 240b include electrodes 242a, 242b, respectively. By way of example, the electrodes 242a, 242b may be of a button or plate-like configuration, wherein the lateral extent thereof is disposed substantially parallel to the second members 270a, 270b, respectively. Where an expanded region of electrode-to-interface is desired (e.g. in electrosurgical pacing electrodes) an added electrode member 248b may be included as shown in the embodiment of FIG. 3B. The electrodes 242a, 242b and optional expansion electrode member 284b may comprise a variety of electrically conductive structures. By way of example only, aluminum/polymer laminates and silver/ silver chloride coated polymer buttons may be employed.

As illustrated in FIGS. 3A and 3B the electrodes 242a, 242b may be disposed, or captured, between conformable layer 280a and first member 270a, and conformable layer 280b and first member 270b, respectively. Consequently, when conformable layers 280a, 280b are adhered to a patient, contemporaneous positioning of the electrode assemblies 240a, 240b and fluid containing layers of the pads 210a, 210b is achieved. Further, electrical energy receipt by electrode assemblies 240a, 240b may be enhanced. That is, the provision of electrically conductive conformable layers 280a, 280b that cover, surround and extend laterally away from the electrode assemblies 240a, 240b, allows the electrode assemblies 240a, 240b to collect electrical energy from a patient region that extends beyond the mere "foot print" of the electrodes 242a, 242b. As such, layers 280a, 280b may yield enhanced electrode performance and facilitate reduced electrode configurations.

Of note, the electrode assemblies 240a, 240b further include electrical connectors 244a, 244b, respectively, which extend through the fluid containing layers (e.g. in opposing relation to electrodes 242a, 242b). The electrical connectors 244a, 244b are surrounded by rib or dimple members 262a, 262b, or some other member for insulating and isolating such connectors 244a, 244b, as they extend through the fluid containing layers. Terminal port members 246a, 246b connected to connectors 244a, 244b are provided on the exposed side of fluid containing layers for selective interconnection (e.g. snap on/off) to the ends of signal cable lines (e.g. such as cable line 300 shown by phantom lines in FIGS. 3A and 3B).

Figure 4:
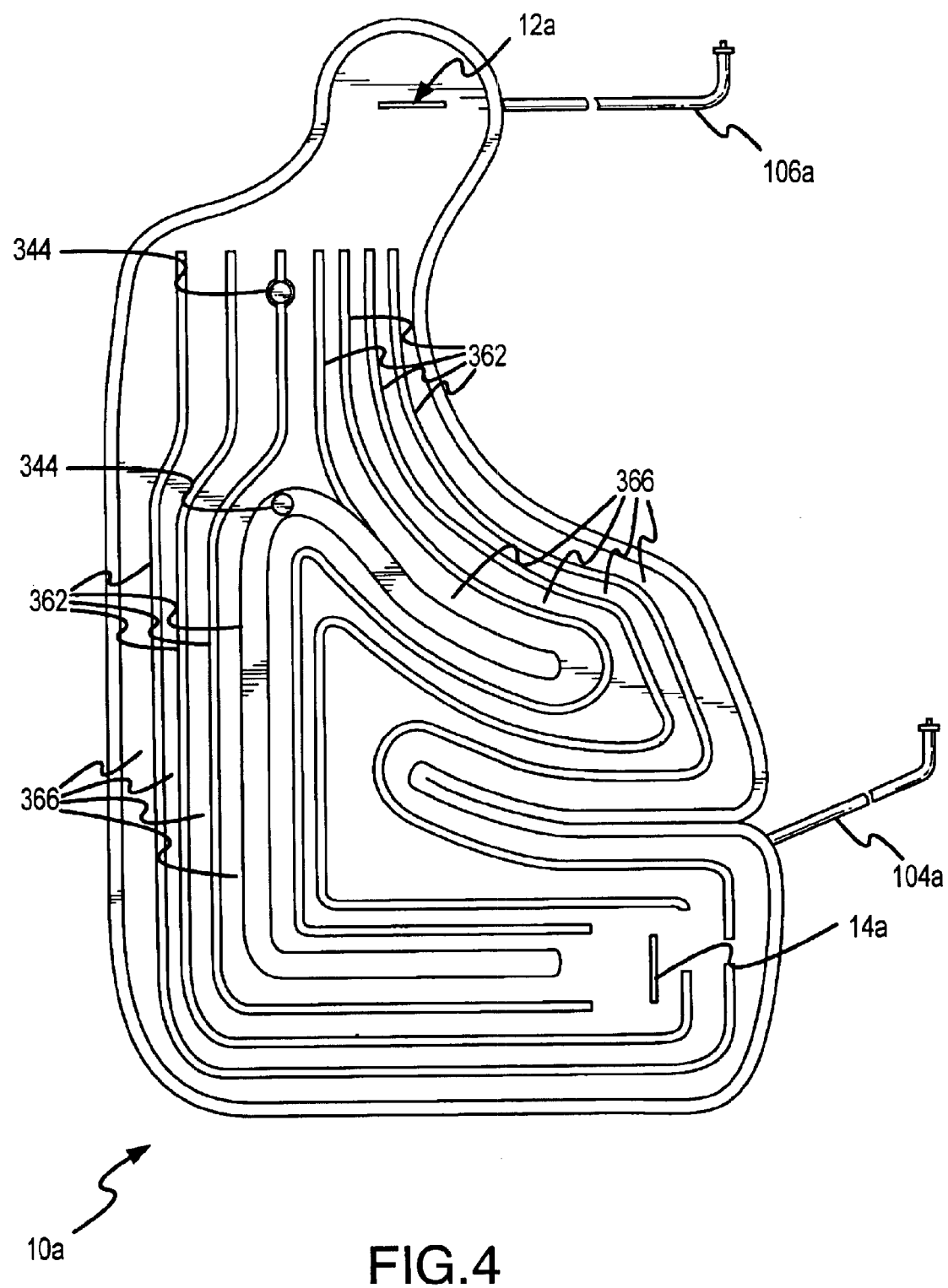
FIG. 4 is an internal plan view of a fluid containing layer of the right back pad embodiment of FIG. 1.

Applying the teachings of FIGS. 3A and 3B, reference is now made to FIG. 4 which illustrates a fluid containing layer of the right back pad 10a of the FIG. 1 and FIG. 2 embodiment. As shown, a number of rib members 362 define fluid channels 366 that extend between the inlet port 12a and outlet port 14a. During use, thermally regulated fluid is circulated between ports 12a and 14a through the channels 366. As further shown, electrical connectors 344 of electrode assemblies 20a, 30a extend through the fluid containing layer and are surrounded by an insulating portion of the material defining corresponding ones of the rib members 362. While not shown, a conformable layer as described above may extend across the substantial entirety of the patient facing side of the pad 10a.

Figure 5:
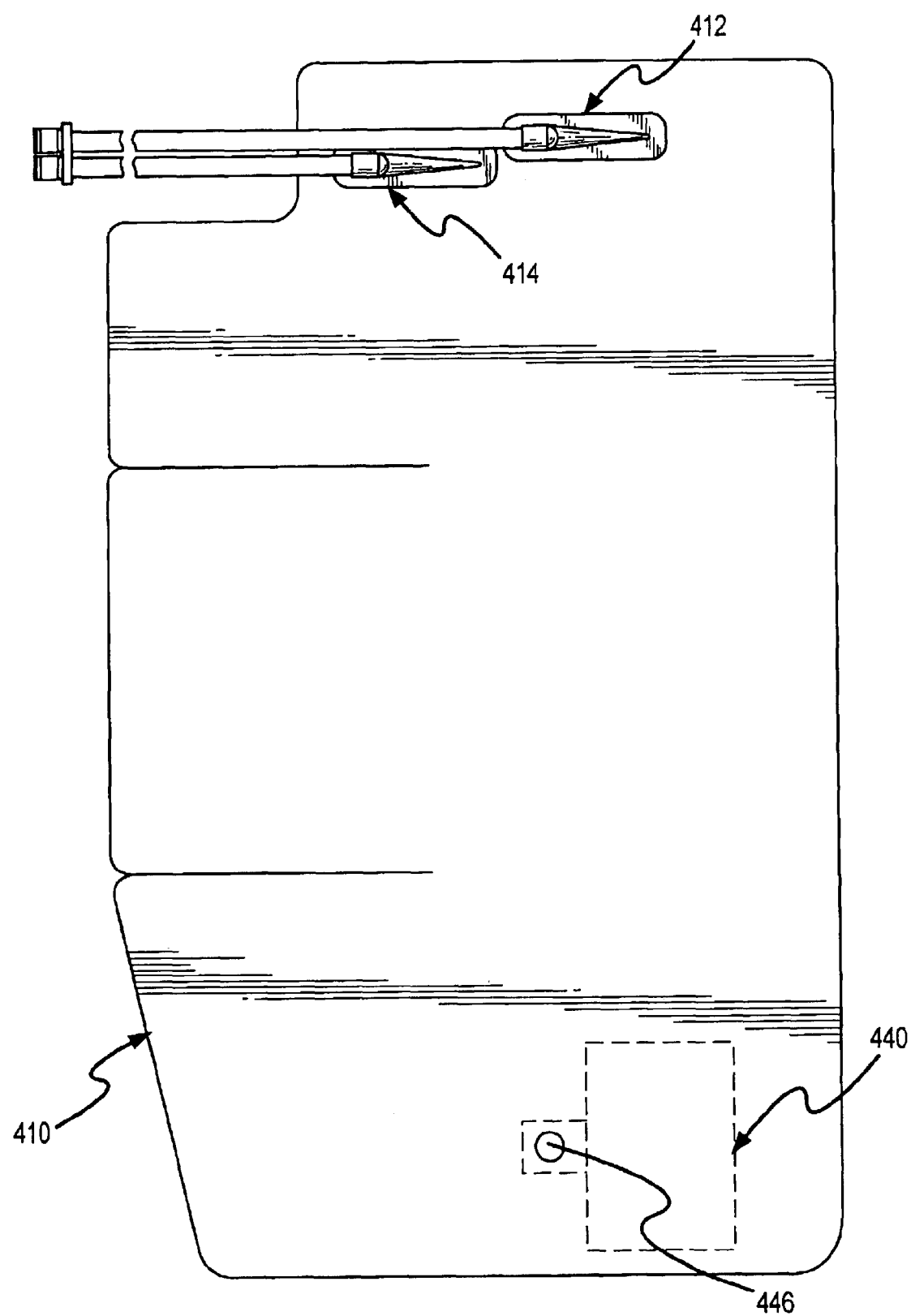
FIG. 5 is another right back pad embodiment of the present invention.
Figure 6:
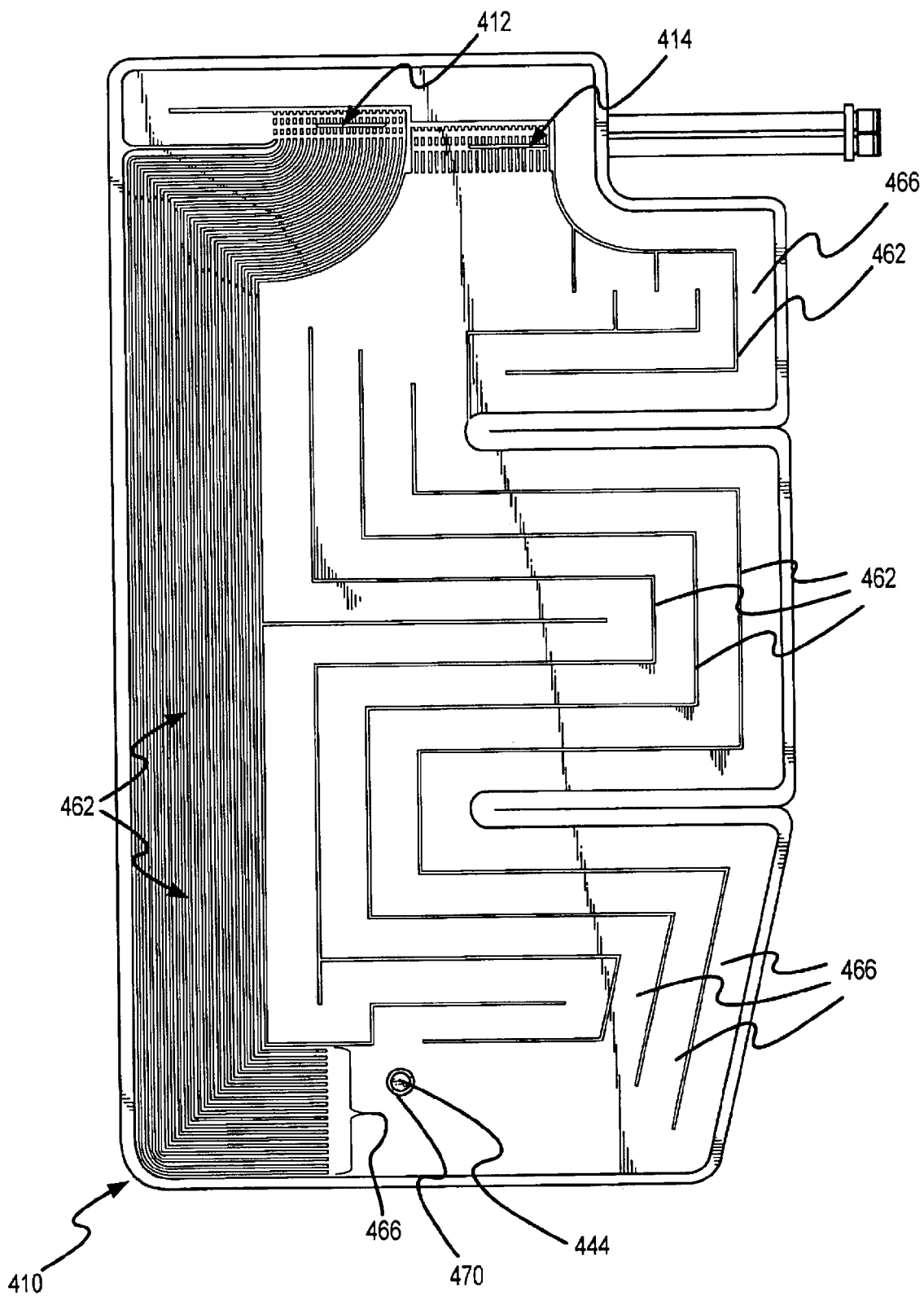
FIG. 6 is an internal plan view of a fluid containing layer of the right back pad embodiment of FIG. 5.

FIGS. 5 and 6 illustrate another right back pad embodiment. As shown in FIG. 5, the back pad 410 includes fluid ports 412, 414 for circulating fluid through the pad 410 during use. The back pad 410 further includes an exemplary electrode assembly 440 having a terminal port member 446 disposed for ready access, as per in electrode assembly 40 noted hereinabove. As shown in FIG. 6, a fluid containing layer of back pad 410 includes a number of rib members 462 defining fluid channels 466 of various configurations. Such channels 466 pass fluid between ports 412, 414. As further illustrated, an electrical connector 444 of the exemplary electrode assembly 440 is surrounded by an insulating member 470. Such material may integrally define the rib members 462, insulating member 420 and a dimple matrix that extends across portions of the fluid containing layer. Again, while not shown, a conformable layer as described above may across the substantial entirety of the patient facing side of the pad 410.

The embodiments described above are for exemplary purposes only and are not intended to limit the scope of the present invention. Various adaptations, modifications and extensions will be apparent to those skilled in the art and are intended to be within the scope of the invention as defined by the claims which follow.

What is claimed is:

1. A medical pad, comprising:
   a fluid containing layer for containing a thermal exchange fluid circulated therethrough, wherein said medical pad is operable for thermal exchange with a patient through a first side of said fluid containing layer; and,
   an external electrode interconnected to said fluid containing layer on said first side thereof, said external electrode being located to transcutaneously receive electrical energy from a patient without passage of such electrical energy through a thermal exchange fluid circulated through said fluid containing layer.

2. A medical pad as recited in claim 1, further comprising:
   an electrical connector electrically connected to said external electrode and extending through said fluid containing layer to a second side thereof.

3. A medical pad as recited in claim 2, said electrical connector comprising:
   a port for electrical interconnection to a signal cable.

4. A medical pad as recited in claim 2, wherein said electrical connector extends through said second side of said fluid containing layer at an exit location within a predetermined area having open-access when said medical pad is positioned on a patient in a predetermined manner.

5. A medical pad as recited in claim 4, wherein said external electrode is provided so that a portion thereof is disposed in opposing relation to said exit location.

6. A medical pad as recited in claims 2, further comprising:
   an insulator surrounding said electrical connector through said fluid containing layer.

7. A medical pad as recited in claim 1, wherein said electrode is one of a group consisting of:
   an electrosurgical return electrode;
   a defibrillation electrode;
   an electrocardiogram electrode; and,
   a pacing electrode.

8. A medical pad as recited in claim 1, further comprising:
   a plurality of different electrodes interconnected to said fluid circulation layer on said first side thereof at locations selected in relation to corresponding functions thereof.

9. A medical pad as recited in claim 1, wherein said external electrode is located outside of said fluid containing layer.

10. A medical pad, comprising:
    a fluid containing layer for containing a thermal exchange fluid circulated therethrough, wherein said medical pad is operable for thermal exchange with a patient through a first side of said fluid containing layer;
    an external electrode interconnected to said fluid containing layer on said first side thereof, said external electrode being located to transcutaneously receive electrical energy from a patient; and,
    an adhesive surface, extending over at least a portion of said first side of said fluid circulation layer, for contacting a patient.

11. A medical pad as recited in claim 10, wherein said adhesive surface substantially covers said external electrode.

12. A medical pad as recited in claim 10, further comprising:
    a conformable layer disposed on said first side of said fluid containing layer, said conformable layer being thermally and electrically conductive, and said conformable layer defining said adhesive surface.

13. A medical pad as recited in claim 12, a conformable layer comprising:
    material suspended in a matrix defined by a second material.

14. A medical pad as recited in claim 13, wherein said first material comprises a liquid and said second material comprises a polymer.

15. A medical as recited in claim 14, wherein said liquid further comprising electrolyte.

16. A medical pad as recited in claim 12, wherein said conformable layer comprises a hydrogel material.

17. A medical pad as recited in claim 12, wherein said external electrode is located between said conformable layer and said fluid circulation layer.

18. A medical pad as recited in claim 12, wherein said electrode is of a plate-like configuration.

19. A medical pad as recited in claim 17, wherein said conformable layer covers, surrounds and extends laterally away from said external electrode.

20. A medical pad comprising:
    a fluid containing layer for containing a thermal exchange fluid circulated therethrough, wherein said medical pad is operable for thermal exchange with a patient through a first side of said fluid containing layer;
    a conformable layer disposed on said first side of said fluid containing layer, said conformable layer being thermally and electrically conductive and having an adhesive surface for engaging a patient; and,
    an external electrode, located between said fluid containing layer and at least a portion of said conformable layer, for receiving electrical energy from a patient through said conformable layer, said external electrode being adapted to transcutaneously receive electrical energy from a patient.

21. A medical pad as recited in claim 20, wherein said conformable layer, covers, surrounds and extends laterally away from said external electrode.

22. A medical pad as recited in claim 21, wherein said external electrode is one of a group consisting of:
    an electrosurgical return electrode;
    a defibrillation electrode;
    an electrocardiogram electrode; and,
    a pacing electrode.

23. A medical pad as recited in claim 22, wherein said conformable layer comprises a hydrogel material.

24. A medical pad as recited in claim 23, wherein said hydrogel material includes an electrolyte.

25. A medical pad as recited in claim 24, wherein said electrolyte is selected from a group consisting of:
- magnesium chloride;
- sodium chloride;
- ammonium acetate;
- magnesium acetate; and,
- magnesium sulfate.

26. A medical pad as recited in claim 20, further comprising:
- an electrical connector electrically connected to said external electrode and extending through said fluid containing layer to an exposed second side thereof; and,
- an insulator surrounding said electrical connector through said fluid containing layer.

27. A medical pad as recited in claim 26, said electrical connector comprising:
- a port for electrical connection to a signal cable.

28. A medical pad as recited in claim 20, wherein said external electrode is located to transcutaneously receive electrical energy from a patient without passage of such electrical energy through a thermal exchange fluid circulated through said fluid containing layer.

29. A medical pad as recited in claim 28, wherein said external electrode is located outside of said fluid containing layer.

30. A method for use in a medical procedure, comprising:
- positioning a medical pad on a patient, said medical pad having a fluid containing layer for containing a fluid circulated therethrough to achieve thermal exchange with a patient through a first side of said fluid containing layer; and,
- locating at least one external electrode relative to said patient contemporaneous with said positioning step, said at least one external electrode being interconnected to said first side of said fluid containing layer; and,
- transcutaneously receiving electrical energy at said at least one external electrode from said patient.

31. A method as recited in claim 30, wherein said electrical energy is transcutaneously received without passage through a thermal exchange fluid circulated through said fluid containing layer.

32. A method as recited in claim 31, wherein said external electrode is located outside of said fluid containing layer.

33. A method as recited in claim 30, wherein said positioning step includes:
- adhering said medical pad to said patient.

34. A method as recited in claim 33, wherein said medical pad includes an adhesive surface that extends over and about at least a portion of said at least one external electrode.

35. A method as recited in claim 34, wherein said adhesive surface is defined by a conformable layer that is thermally and electrically conductive.

36. A method as recited in claim 35, wherein said electrical energy is transcutaneously received through said conformable layer from a patient region that extends beyond a footprint of said external electrode.

37. A method as recited in claim 30, wherein an electrical connector is electrically connected to said at least one external electrode and extends through the fluid containing layer to a second side thereof, and wherein the method further includes:
- interconnecting an electrical cable with said electrical connector on said second side.

38. A method as recited in claim 32, wherein said interconnecting step is completed after said positioning step.

39. A method as recited in claim 30, wherein said at least one electrode is one of a group consisting of:
- an electrosurgical return electrode;
- a defibrillation electrode;
- an electrocardiogram electrode; and,
- a pacing electrode.

* * * * *

UNITED STATES PATENT AND TRADEMARK OFFICE
CERTIFICATE OF CORRECTION

PATENT NO. : 6,799,063 B2
DATED : September 28, 2004
INVENTOR(S) : Carson

It is certified that error appears in the above-identified patent and that said Letters Patent is hereby corrected as shown below:

Column 8,
Line 24, before the word "material", insert -- a first --;
Line 30, delete "comprising", and insert therefor -- comprises an --;
Line 57, delete "layer,", and insert therefor -- layer --.

Signed and Sealed this

Twenty-fifth Day of October, 2005

JON W. DUDAS
*Director of the United States Patent and Trademark Office*